(12) United States Patent
Farida et al.

(10) Patent No.: US 9,376,374 B2
(45) Date of Patent: Jun. 28, 2016

(54) PROCESS FOR PREPARING CIS-ALKOXY-SUBSTITUTED SPIROCYCLIC PHENYLACETYLAMINO ACID ESTERS AND CIS- ALKOXY-SUBSTITUTED SPIROCYCLIC 1H- PYRROLIDINE-2,4-DIONE DERIVATIVES

(71) Applicants: BAYER INTELLECTUAL PROPERTY GMBH, Monheim (DE); BAYER CROPSCIENCE AG, Monheim (DE)

(72) Inventors: Taraneh Farida, Pulheim-Geyen (DE); Berndt Maiwald, Burscheid (DE); Martin Littmann, Leverkusen (DE); Winfried Etzel, Leichlingen (DE); Rafael Warsitz, Essen (DE); Nicolas Henck, Bonn (DE); Michael Esser, Leverkusen (DE)

(73) Assignee: Bayer Intellectual Property GmbH, Monheim am Rhein (DE)

( * ) Notice: Subject to any disclaimer, the term of this patent is extended or adjusted under 35 U.S.C. 154(b) by 0 days.

(21) Appl. No.: 14/387,249

(22) PCT Filed: Mar. 25, 2013

(86) PCT No.: PCT/EP2013/056318
§ 371 (c)(1),
(2) Date: Sep. 23, 2014

(87) PCT Pub. No.: WO2013/144101
PCT Pub. Date: Oct. 3, 2013

(65) Prior Publication Data
US 2015/0051407 A1    Feb. 19, 2015

(30) Foreign Application Priority Data
Mar. 28, 2012    (EP) .................................... 12161837

(51) Int. Cl.
*C07D 209/54*    (2006.01)
*C07D 263/52*    (2006.01)
*C07C 231/12*    (2006.01)
*C07C 233/52*    (2006.01)

(52) U.S. Cl.
CPC ............. *C07C 231/12* (2013.01); *C07C 233/52* (2013.01); *C07D 209/54* (2013.01); *C07D 263/52* (2013.01); *C07C 2101/14* (2013.01)

(58) Field of Classification Search
None
See application file for complete search history.

(56) References Cited

U.S. PATENT DOCUMENTS 7,638,547 B2    12/2009    Himmler et al.
7,897,803 B2    3/2011    Himmler et al.

FOREIGN PATENT DOCUMENTS

WO    2004007448 A1    1/2004

OTHER PUBLICATIONS

International Search Report from corresponding PCT/EP2013/056318, mailed May 27, 2013.
Harrison et al., "Use of Molecular Sieves in the Methyl Esterification of Carboxylic Acids", Journal of Applied Chemistry, Society of Chemical Industry, London, GB, Bd. 75, Nov. 9, 1968, XP000925894.
Sonntag, "The Reactions of Aliphatic Acid Chlorides", Chemical Reviews, Colgate-Palmolive-Peet Company, Jersey City, New Jersey, Nov. 15, 1952, pp. 237-416.
Bhattacharya, "Isoquinoline Derivatives: Part XVIII—Formation of 1-Alkyl-(or alkaryl or aryl)-3-methyl-7-chloro . . . (or 5-chloro)-isoquinolines", Indian J. Chem. 6, 1968, pp. 341-345.
Organikum, VEB Deutscher Verlag der Wissen•schaften, Berlin 1977, S. 505, 1 page.

*Primary Examiner* — Kamal Saeed
(74) *Attorney, Agent, or Firm* — McBee Moore Woodward Vanik IP, LLC

(57) ABSTRACT

The present invention relates to a novel process for preparing cis-alkoxy-substituted spirocyclic phenylacetylamino acid esters and cis-alkoxy-substituted spirocyclic 1H-pyrrolidine-2,4-dione derivatives, and also to novel intermediates and starting materials which are produced and/or used in the process according to the invention.

15 Claims, No Drawings

PROCESS FOR PREPARING CIS-ALKOXY-SUBSTITUTED SPIROCYCLIC PHENYLACETYLAMINO ACID ESTERS AND CIS- ALKOXY-SUBSTITUTED SPIROCYCLIC 1H- PYRROLIDINE-2,4-DIONE DERIVATIVES

CROSS REFERENCE TO RELATED APPLICATIONS

This application is a §371 National Stage Application of PCT/EP2013/056318, filed Mar. 25, 2013, which claims priority to EP 12161837.5, filed Mar. 28, 2012.

BACKGROUND

1. Field of the Invention

The present invention relates to a novel process for preparing cis-alkoxy-substituted spirocyclic phenylacetylamino acid esters and cis-alkoxy-substituted spirocyclic 1H-pyrrolidine-2,4-dione derivatives, and also to novel intermediates and starting materials which are produced and/or used in the process according to the invention. Cis-alkoxy-substituted spirocyclic phenylacetylamino acid esters are important intermediates for the synthesis of insecticidal/acaricidal active compounds.

2. Description of Related Art

Cis-alkoxy-substituted spirocyclic phenylacetylamino acid esters are known, for example, from WO 04/007448. Cis-alkoxy-substituted spirocyclic phenylacetylamino acid esters of the formula (I) are obtained when cis-amino acid derivatives of the formula (VI)

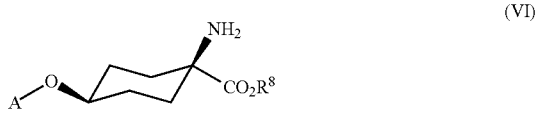

(VI)

are acylated with substituted phenylacetyl halides of the formula (VII)

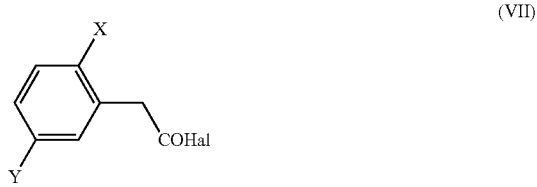

(VII)

(Chem. Reviews 52, 237-416 (1953); Bhattacharya, Indian J. Chem. 6, 341-5, 1968) or when cis-amino acids of the formula (VIII)

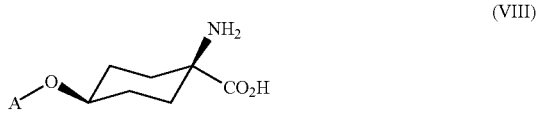

(VIII)

are acylated with substituted phenylacetyl halides of the formula (VII)

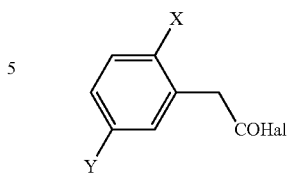

(VII)

according to Schotten-Baumann (Organikum, VEB Deutscher Verlag der Wissenschaften, Berlin 1977, p. 505) and esterified (Chem. Ind. (London) 1568 (1968)).

In the current process, the cis-alkoxy-substituted spirocyclic phenylacetylamino acid (compounds of the formula (IIa)) is extracted with hot chlorobenzene. This solution is esterified with methanol under sulphuric acid catalysis to give compounds of the formula (I) (partial esterification of the compounds of the formula (IIa)). The non-esterified portion is recycled. Since the compounds of the formula (I) do not remain dissolved in chlorobenzene at room temperature, the solvent chlorobenzene is replaced by dimethylacetamide.

Particular disadvantages of this process are the unsatisfactory yield and the high expenditure for the process. Moreover, the solvents chlorobenzene and dimethylacetamide (DMAC) used are reluctantly employed. The disposal of the DMAC-containing waste water is associated with high costs.

SUMMARY

It is an object of the present invention to provide a novel, economically and ecologically favourable process for the selective preparation of cis-alkoxy-substituted spirocyclic phenylacetylamino acid esters. In particular, the process according to the invention should be able to manage with customary solvents. Use may be made of toluene, xylene, alkanes such as n-hexane, n-heptane, n-octane, ethers such as diethyl ether, diisopropyl ether, dibutyl ether, anisole, methyl tert-butyl ether, methyl tert-amyl ether, glycol dimethyl ether, diglycol dimethyl ether, tetrahydrofuran or dioxane, ketones such as acetone, methyl ethyl ketone, methyl isopropyl ketone or methyl isobutyl ketone (MIBK), hydrocarbons such as pentane, hexane, heptane, cyclohexane, methylcyclohexane, benzene, halogenated hydrocarbons such as methylene chloride, chloroform, carbon tetrachloride, chlorobenzene or o-dichlorobenzene, dichloroethane. Preference is given to toluene or xylene. Particular preference is given to xylene.

It has now been found that a mixture of compounds of the formula (I)

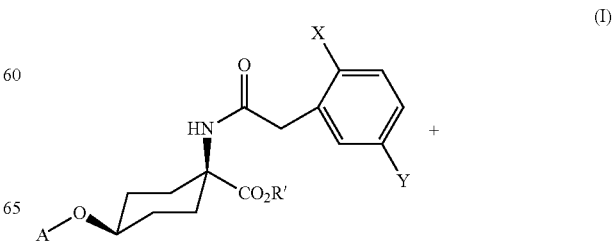

(I)

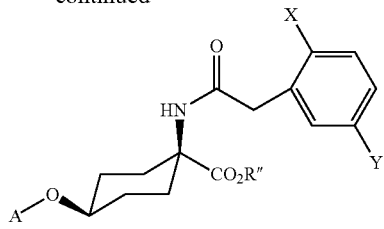

in which
X represents alkyl, halogen, alkoxy, haloalkyl or haloalkoxy,
Y represents hydrogen, alkyl, alkoxy, halogen, haloalkyl or haloalkoxy, where only one of the radicals X or Y may represent haloalkyl or haloalkoxy,
A represents $C_1$-$C_6$-alkyl,
R' represents alkyl,
R" represents alkyl,
is obtained
when initially compounds of the formula (IIa)

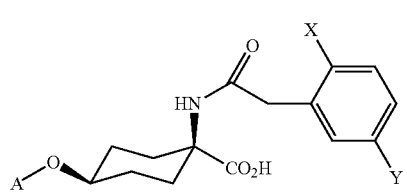

in which X, Y and A have the meanings mentioned above
are converted in the presence of a base into compounds of the formula (IIb)

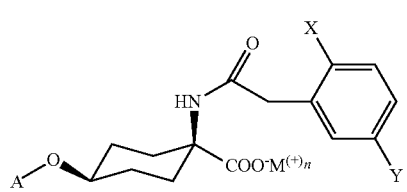

in which X, Y and A have the meanings mentioned above and M represents an alkali metal ion, an ion equivalent of an alkaline earth metal, an ion equivalent of aluminium or an ion equivalent of a transition metal or furthermore
represents an ammonium ion where optionally one, two, three or all four hydrogen atoms may be replaced by identical or different radicals from the groups $C_1$-$C_5$-alkyl, $C_1$-$C_5$-isoalkyl or $C_3$-$C_7$-cycloalkyl, each of which may be mono- or polysubstituted by fluorine, chlorine, bromine, cyano, hydroxy or interrupted by one or more oxygen or sulphur atoms, or furthermore
represents a cyclic secondary or tertiary aliphatic or heteroaliphatic ammonium ion, for example morpholinium, thiomorpholinium, piperidinium, pyrrolidinium, or in each case protonated 1,4-diazabicyclo[2.2.2]octane (DABCO) or 1,5-diazabicyclo[4.3.0]undec-7-ene (DBU), or furthermore
represents a heterocyclic ammonium cation, for example in each case protonated pyridine, 2-methylpyridine, 3-methylpyridine, 4-methylpyridine, 2,4-dimethylpyridine, 2,5-dimethylpyridine, 2,6-dimethylpyridine, 5-ethyl-2-methylpyridine, pyrrole, imidazole, quinoline, quinoxaline, 1,2-dimethylimidazole, 1,3-dimethylimidazolium methylsulphate, or furthermore
represents a sulphonium ion, or furthermore
represents a magnesium halide cation,
n represents the number 1 or 2
and reacted further with compounds of the formula (III)

in which R' has the meanings given above
and Hal represents halogen,
to give compounds of the formula (IV)

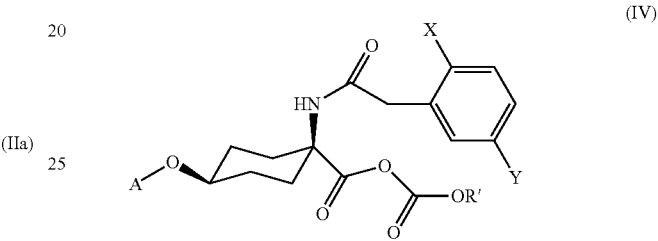

in which X, Y, A and R' have the meanings mentioned above, and these are further cyclized to compounds of the formula (IX)

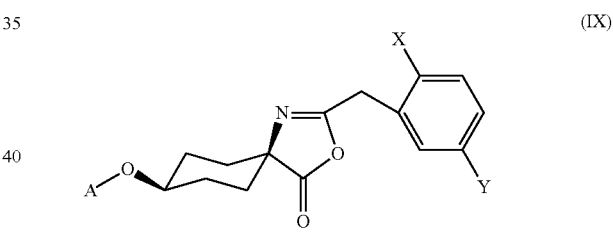

in which X, Y and A have the meanings given above,
and these for their part are reacted with compounds of the formula (V)

R"—OH   (V)

in which
R" has the meanings given above,
to give a mixture of compounds of the formula (I).

DETAILED DESCRIPTION OF A PREFERRED EMBODIMENT

In the formulae (I), (I'), (I"), (IIa), (IIb), (III), (IV), (V), (IX), (X) and (XI), X preferably represents chlorine, bromine, methyl, ethyl, propyl, trifluoromethyl, methoxy, difluoromethoxy or trifluoromethoxy,
Y preferably represents hydrogen, chlorine, bromine, methoxy, methyl, ethyl, propyl, trifluoromethyl or trifluoromethoxy, where only one of the radicals X or Y may represent trifluoromethyl, trifluoromethoxy or difluoromethoxy,
A preferably represents $C_1$-$C_6$-alkyl,
Hal preferably represents chlorine, bromine, fluorine, iodine, R' preferably represents $C_1$-$C_6$-alkyl,
R" preferably represents $C_1$-$C_6$-alkyl,
X particularly preferably represents chlorine, bromine, methyl, ethyl, methoxy, trifluoromethyl, trifluoromethoxy or difluoromethoxy,
Y particularly preferably represents chlorine, bromine, methyl, ethyl, propyl, methoxy, trifluoromethyl or trifluoromethoxy, where only one of the radicals X or Y may represent trifluoromethyl, trifluoromethoxy or difluoromethoxy,
A particularly preferably represents $C_1$-$C_4$-alkyl,
Hal particularly preferably represents chlorine, bromine or fluorine,
R' particularly preferably represents $C_1$-$C_4$-alkyl,
R" particularly preferably represents $C_1$-$C_4$-alkyl,
X very particularly preferably represents chlorine, bromine, methyl or trifluoromethyl (in particular chlorine, bromine or methyl),
Y very particularly preferably represents chlorine, bromine or methyl, (in particular methyl),
A very particularly preferably represents methyl, ethyl, propyl, butyl or isobutyl, (in particular methyl or ethyl),
Hal very particularly preferably represents chlorine or bromine,
R' very particularly preferably represents methyl, ethyl, propyl, butyl or isobutyl,
R" very particularly preferably represents methyl, ethyl, propyl, butyl or isobutyl,
X most preferably represents methyl,
Y most preferably represents methyl,
A most preferably represents methyl,
Hal most preferably represents chlorine,
R' most preferably represents methyl or ethyl (especially ethyl),
R" most preferably represents methyl or ethyl (especially methyl).

In the formula (IIb),
M preferably represents lithium, sodium, potassium, caesium, magnesium, calcium or represents an ammonium ion in which optionally one, two, three or all four hydrogen atoms may be replaced by identical or different radicals from the groups $C_1$-$C_5$-alkyl, $C_1$-$C_5$-isoalkyl or $C_3$-$C_7$-cycloalkyl, each of which may be mono- or polysubstituted by fluorine, chlorine, bromine, cyano, hydroxy and n represents the number 1 or 2,
M particularly preferably represents lithium, sodium, potassium, caesium, magnesium or calcium and n represents the number 1 or 2,
M very particularly preferably represents lithium, sodium, potassium or caesium and n represents the number 1,
M most preferably represents sodium and n represents the number 1.

The abovementioned general or preferred radical definitions or illustrations can be combined with one another as desired, i.e. including combinations between the respective ranges and preferred ranges. They apply both to the end products and, correspondingly, to precursors and intermediates.

In the definitions of the symbols given in the formulae above, collective terms were used which are generally representative of the following substituents:
Halogen: fluorine, chlorine, bromine and iodine.
Alkyl: saturated straight-chain or branched hydrocarbons having 1 to 8 carbon atoms, for example $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl; heptyl, octyl.
Haloalkyl: straight-chain or branched alkyl groups having 1 to 8 carbon atoms, where some or all of the hydrogen atoms in these groups may be replaced by halogen atoms as mentioned above, for example $C_1$-$C_3$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl and 1,1,1-trifluoroprop-2-yl.

Scheme 1:
The course of the process according to the invention is represented by the reaction scheme below:

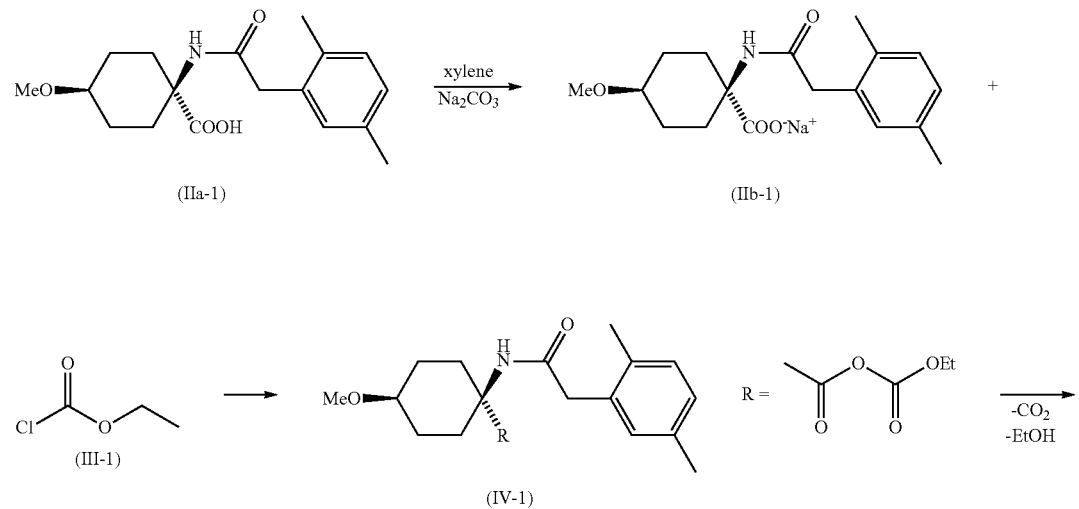

-continued
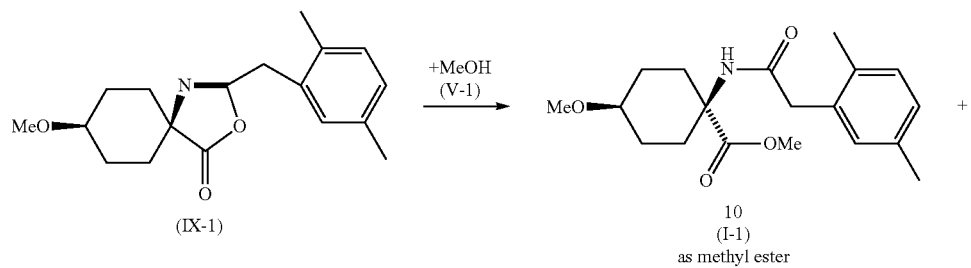
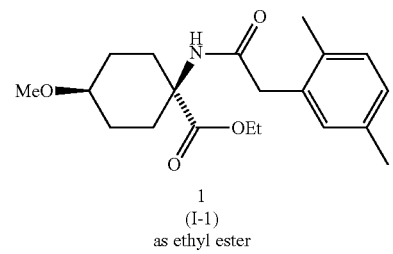
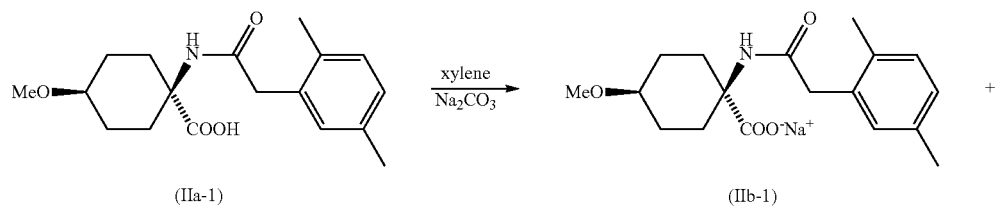
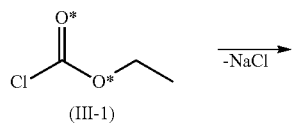
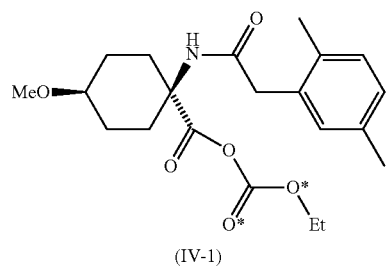
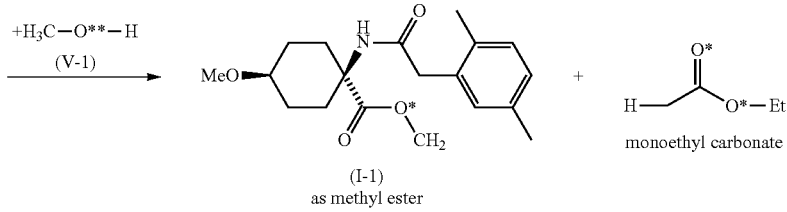

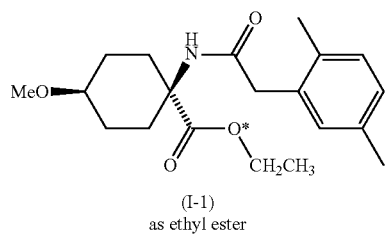

(I-1)
as ethyl ester

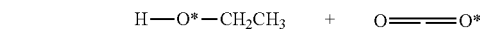

The indices * and ** at the oxygen atom in Scheme 1 are to illustrate the course of the reaction.

Depending on the type of alcohol and the amount of alcohol (compounds of the formula (V)), an ester mixture of the formula (I) is obtained (in Scheme 1: methyl ester and ethyl ester in a ratio of 10:1).

Moreover, it has been found that compounds of the formula (I')

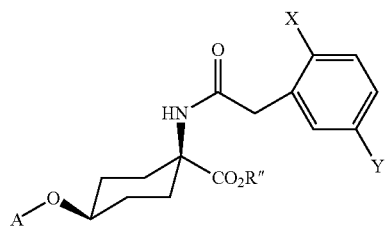

(I')

in which X, Y, A and R″ have the meanings given above, are obtained
when initially compounds of the formula (IIa)

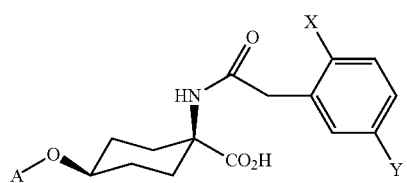

(IIa)

in which X, Y and A have the meanings mentioned above are converted in the presence of a base into compounds of the formula (IIb)

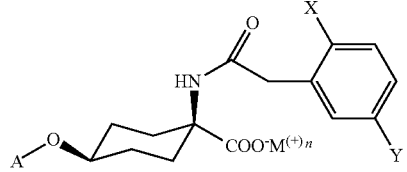

(IIb)

in which X, Y, A, M and n have the meanings mentioned above and reacted further with compounds of the formula (III)

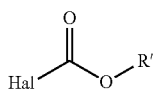

(III)

in which R′ has the meanings given above
and Hal represents halogen,
to give compounds of the formula (IV)

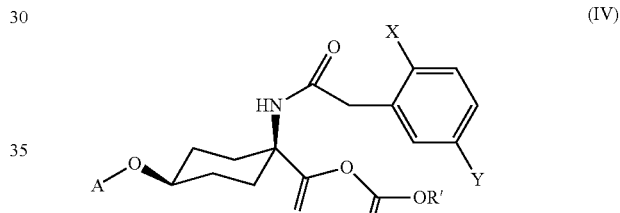

(IV)

in which X, Y, A and R′ have the meanings mentioned above
these are further cyclized to compounds of the formula (IX)

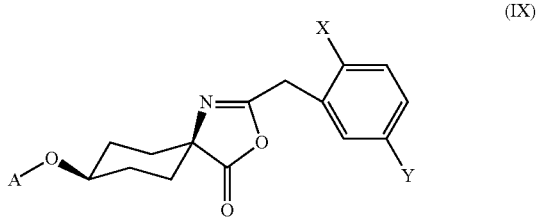

(IX)

in which X, Y and A have the meanings given above,
and these for their part are reacted with compounds of the formula (V)

R″—OH    (V)

in which
R″ has the meanings given above,
to give compounds of the formula (I′).

Scheme 2:
The course of the process according to the invention is represented by the reaction scheme below:

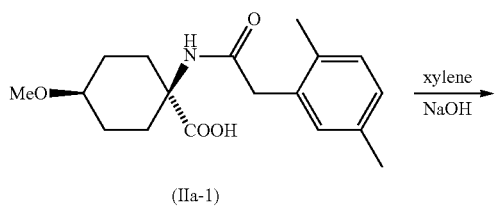

(IIa-1)

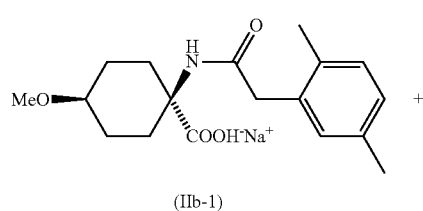

(IIb-1)

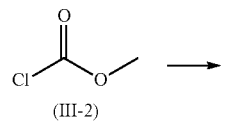

(III-2)

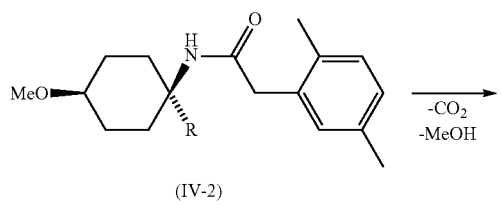

(IV-2)

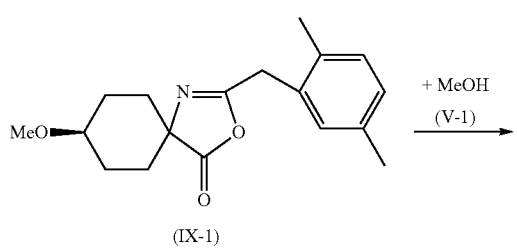

(IX-1)

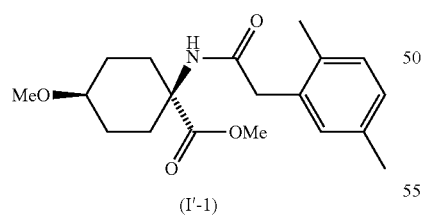

(I'-1)

R = 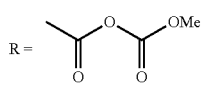

It is known that the compounds of the formula (I) or (I') can be condensed intramolecularly in the presence of a diluent and in the presence of a base to give cis-alkoxy-substituted spirocyclic 1H-pyrrolidine-2,4-dione derivatives of the formula (X)

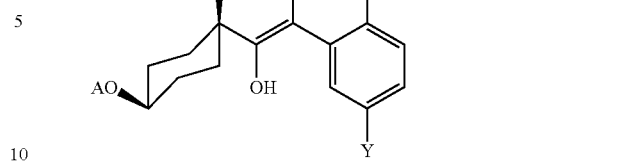
(X)

in which
A, X and Y have the meanings given above
(WO 04/007448).

It has now been found that the compounds of the formula (X)

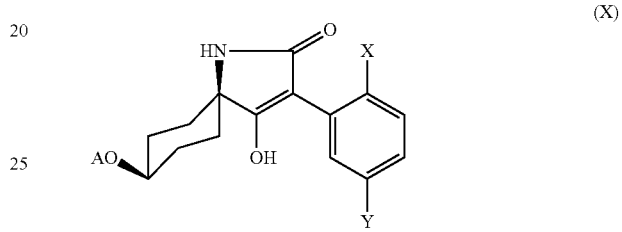
(X)

in which
A, X and Y have the meanings given above,
are obtained in a one-pot reaction
by converting compounds of the formula (IIa)

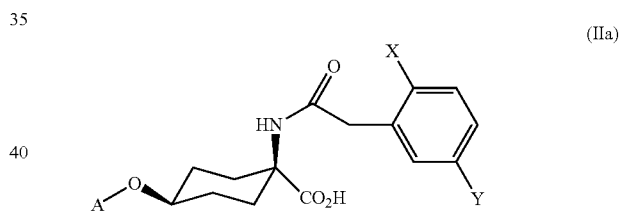
(IIa)

in which X, Y and A have the meanings mentioned above,
in the presence of a base
into compounds of the formula (IIb)

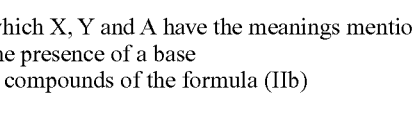
(IIb)

in which X, Y, A, M and n have the meanings mentioned above
and reacting with compounds of the formula (III)

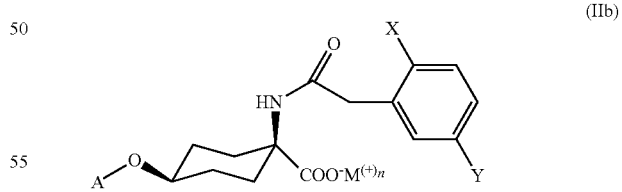
(III)

in which R' has the meanings given above and Hal represents halogen,
in the presence of a strong base of the formula (XI)

$$ZLR'' \quad (XI)$$

where
Z represents an alkali metal ion (preferably represents lithium, sodium or potassium, particularly preferably sodium or potassium, very particularly preferably sodium),
L represents oxygen or sulphur (preferably oxygen),
R" has the meanings given above,
preference is given, for example, to alkoxides or thiolates which can be employed either as a solid or as a solution, for example NaOMe in solid form or as a solution in methanol, NaOEt in solid form or as a solution in ethanol, NaSMe in solid form or as a solution in methanol, NaSEt in solid form or as a solution in ethanol).

Scheme 3
The course of the process according to the invention is represented by the reaction scheme below:
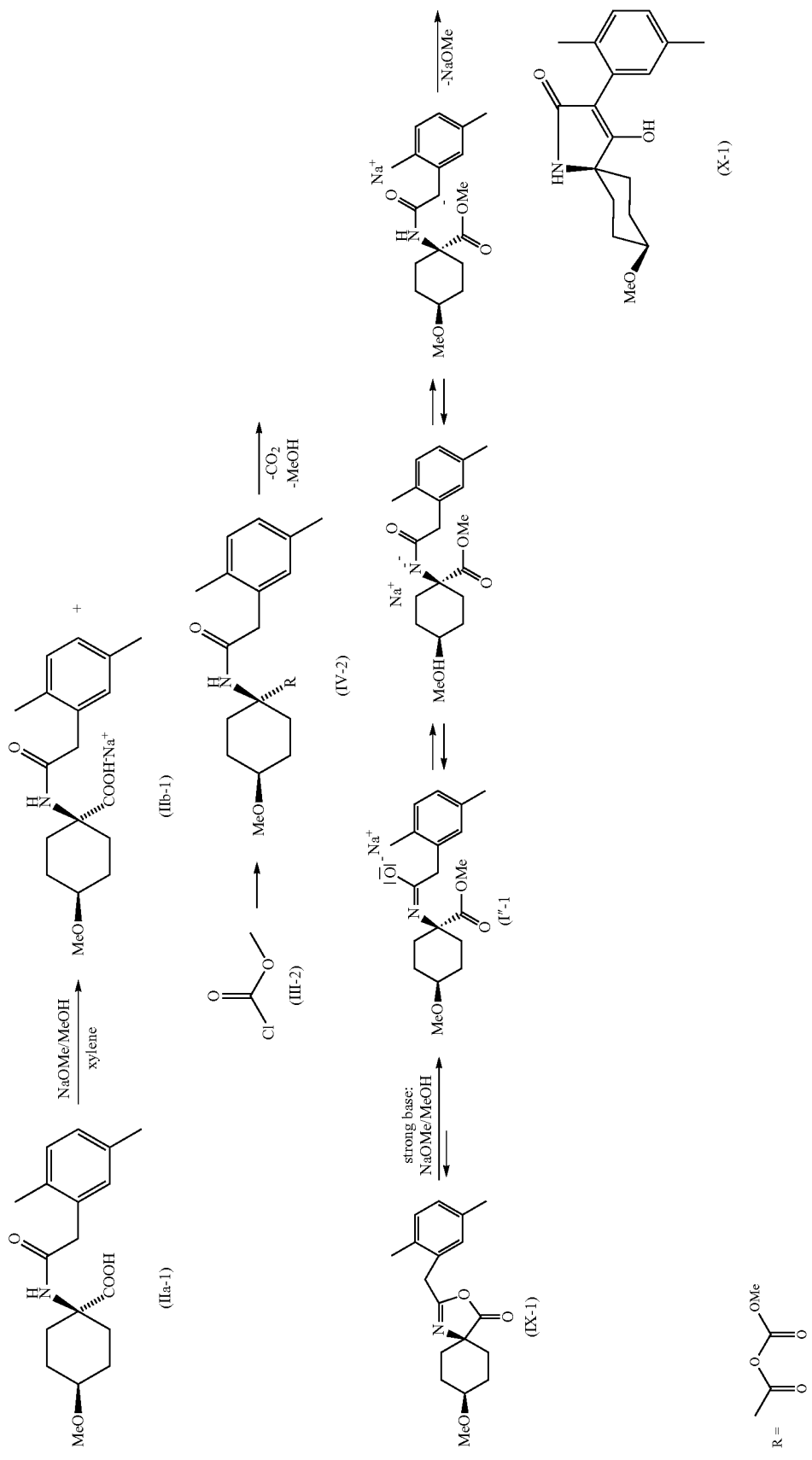

Surprisingly, by the process according to the invention, the compounds of the formula (X) can be prepared in a more simple manner, in a one-pot process, without isolation of the intermediates, in higher purity and in better yield.

The compounds of the formulae (I') and (I) are known (WO 04/007448) or can be prepared by the processes described therein.

The compounds of the formula (I'') are novel.

The compounds of the formula (IIa) are known (WO 04/007448) or can be prepared by the processes described therein.

The compounds of the formula (IIb) are novel.

The compounds of the formula (III) are commercially available.

The compounds of the formula (IV) are novel.

The compounds of the formula (V) are commercially available.

The compounds of the formula (IX) are novel.

The compounds of the formula (X) are known (WO 04/007448) or can be prepared by the processes described therein.

The compounds of the formula (XI) are commercially available.

Owing to the cis/trans isomer ratio of the compounds of the formula (IIa) employed for the preparation process, the compounds of the formulae (I) and (I') and (I''), (IIb), (IV), (IX) and (X) are obtained in the form of cis/trans isomer mixtures, where in the process according to the invention mainly the cis-isomer is formed.

The process is characterized in that compounds of the formula (IIa) having a high proportion of cis isomer are converted in the presence of a base and in the presence of solvents into the corresponding salt of the formula (IIb). After azeotropic drying of the reaction mixture, the compounds of the formula (IIb) are reacted with compounds of the formula (III) to give intermediates of the formula (IV). These cyclize to compounds of the formula (IX).

The compounds of the formula (IX) can be present in two tautomeric forms:

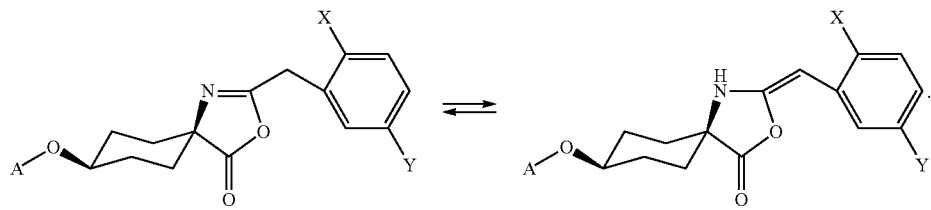

The compounds can be present either as mixtures or in the form of their pure tautomers. Mixtures can, if desired, be separated using physical methods, for example chromatographic methods.

For the sake of clarity, hereinbelow only one of the possible tautomers is shown in each case. This does not preclude that the compounds may optionally be present in the form of the tautomer mixtures or in the respective other tautomeric form.

The compounds of the formula (IX) are converted in the presence of an alcohol of the formula (V) into compounds of the formula (I) or (I').

When carrying out the process according to the invention, the reaction temperature for preparing the compounds of the formula (IIb) may be varied. In general, the process is carried out at temperatures between 20° C. and 110° C., preferably between 80° C. and 85° C. Preference is also given to a temperature of 25° C. Likewise, preference is given to a temperature of 70° C.

The base employed can be an alkoxide, either as a solid or as a solution, for example NaOMe as a solid or as a solution in methanol, NaOEt as a solid or NaOEt as a solution, sodium bicarbonate, sodium hydroxide or potassium hydroxide, alkaline earth metal hydroxides such as calcium hydroxide, alkali metal carbonates or alkali metal alkoxides such as sodium carbonate or potassium carbonate, sodium tert-butoxide or potassium tert-butoxide. In the bases mentioned, sodium may be replaced by potassium. Preference is given to sodium carbonate. Preference is also given to 30% strength sodium methoxide in methanol. Likewise, preference is given to sodium hydroxide.

Suitable for use as solvents are toluene, xylene, alkanes such as n-hexane, n-heptane, n-octane, ethers such as diethyl ether, diisopropyl ether, dibutyl ether, anisole, methyl tert-butyl ether, methyl tert-amyl ether, glycol dimethyl ether, diglycol dimethyl ether, tetrahydrofuran or dioxane, ketones such as acetone, methyl ethyl ketone, methyl isopropyl ketone or methyl isobutyl ketone (MIBK), hydrocarbons such as pentane, hexane, heptane, cyclohexane, methylcyclohexane, benzene, halogenated hydrocarbons such as methylene chloride, chloroform, carbon tetrachloride, chlorobenzene or o-dichlorobenzene, dichloroethane. Preference is given to toluene or xylene. Particular preference is given to xylene.

When carrying out the process according to the invention, the reaction temperature for preparing the compounds of the formula (IV) may be varied. In general, the process is carried out at temperatures between 20° C. and 100° C., preferably between 65° C. and 70° C., preferably also at 70° C.

When carrying out the process according to the invention, the reaction components of the formula (III) are generally employed in equimolar to about double equimolar amounts.

The one-pot process is characterized in that compounds of the formula (IIa) having a high proportion of cis-isomer are converted in the presence of a base and in the presence of solvents into the corresponding salt of the formula (IIb), which reacts with compounds of the formula (III) to give compounds of the formula (IV). In this reaction, the compounds of the formula (IX) are formed by cyclization. These compounds can be cleaved with a strong base of the formula (XI) (nucleophilic addition) to give compounds of the formula (I'')

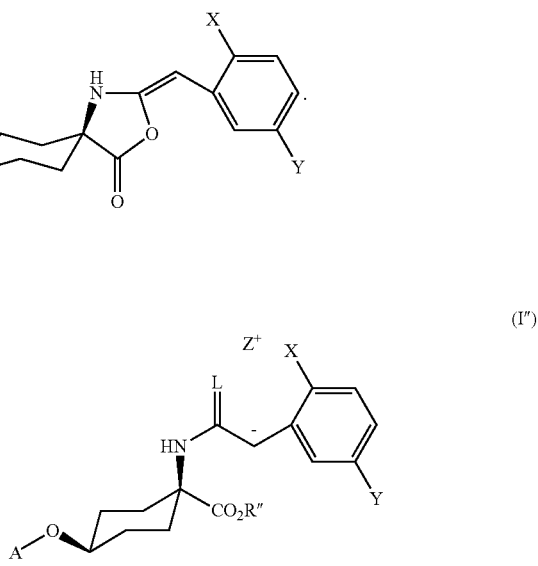

in which X, Y, A, L, Z and R'' have the meanings given above, and cyclized to give compounds of the formula (X).

It is furthermore possible for the compounds of the formula (IV) in the presence of a strong base to react directly to compounds of the formula (X).

The compounds of the formula (I″) can be present in the following tautomeric forms:

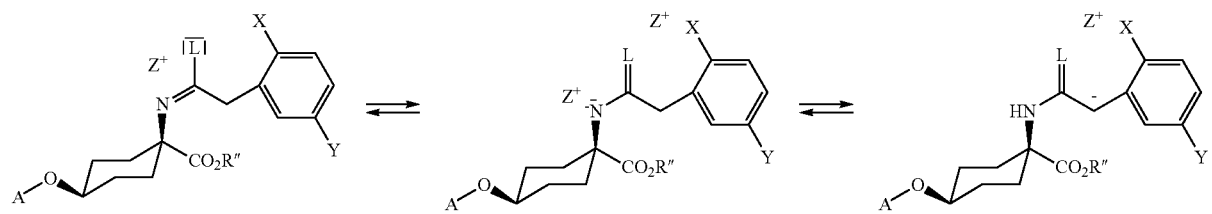

The compounds can be present either as mixtures or in the form of their pure tautomers. Mixtures can, if desired, be separated using physical methods, for example chromatographic methods.

For the sake of clarity, hereinbelow only one of the possible tautomers is shown in each case. This does not preclude that the compounds may optionally be present in the form of the tautomer mixtures or in the respective other tautomeric form.

When carrying out the one-pot process according to the invention, the reaction temperature for preparing the compounds of the formula (X) from compounds of the formula (IIa) may be varied. In general, the process is carried out at temperatures between 20° C. and 110° C., preferably between 60° C. and 85° C. Preference is given to a temperature of 60° C.

The bases employed can be the compounds mentioned above.

The strong base of the formula (XI) employed can, for example, be an alkoxide or thiolate, either as a solid or as a solution, for example NaOMe in solid form or as a solution in methanol, NaOEt in solid form or as a solution in ethanol, NaSMe in solid form or as a solution in methanol, NaSEt in solid form or as a solution in ethanol. Preference is given to NaOMe as a solution in methanol.

Suitable for use as solvents are toluene, xylene, alkanes such as n-hexane, n-heptane, n-octane, ethers such as diethyl ether, diisopropyl ether, dibutyl ether, anisole, methyl tert-butyl ether, methyl tert-amyl ether, glycol dimethyl ether, diglycol dimethyl ether, tetrahydrofuran or dioxane, ketones such as acetone, methyl ethyl ketone, methyl isopropyl ketone or methyl isobutyl ketone (MIBK), hydrocarbons such as pentane, hexane, heptane, cyclohexane, methylcyclohexane, benzene, halogenated hydrocarbons such as methylene chloride, chloroform, carbon tetrachloride, chlorobenzene or o-dichlorobenzene, dichloroethane. Preference is given to toluene or xylene. Particular preference is given to xylene.

When carrying out the process according to the invention, the reaction components of the formula (III) are generally employed in equimolar to about double equimolar amounts.

PREPARATION EXAMPLES

Example 1

Complete Esterification

At 80-85° C., 25.7 g (0.24 mol) of sodium carbonate 99% are added to 514 g (0.59 mol) of cis-N-[(2,5-dimethyl)phenylacetyl]-1-amino-4-methoxycyclohexanecarboxylic acid (IIa-1) (37% strength in xylene). The water is removed by azeotropic distillation. At 65° C., 100 g (3.12 mol) of methanol are added. Over a period of about 2 hours, 80.5 g (0.72 mol) of ethyl chloroformate (III-1) 97% are metered in at 65-70° C., with carbon dioxide being formed as waste gas. The reaction mixture is stirred at 70° C. for a further 2 hours. The alcohols (ethanol and methanol) are removed at 300 mbar and 70° C. After addition of 150 g (8.33 mol) of water at 70° C., the lower aqueous phase is separated off. 100 g (5.56 mol) of water and 7 g (0.08 mol) of sodium bicarbonate are added at 70° C., and the lower aqueous phase is separated off. Azeotropic drying gives the target product (I-1) as a mixture (methyl and ethyl esters) in xylene. The product can be isolated at room temperature by filtration and drying. In a xylene/methanol mixture, the product (I-1) remains in solution. The yield is 98% of theory based on the compound of the formula (IIa-1).

Example 2

Complete Esterification

At 25° C., 113.5 g (0.63 mol) of 30% sodium methoxide in methanol are added to 496 g (0.61 mol) cis-N-[(2,5-dimethyl) phenylacetyl]-1-amino-4-methoxycyclohexanecarboxylic acid (IIa-1) (39% in xylene). Over a period of 2 hours, 87 g (0.78 mol) of ethyl chloroformate (III-1) 97% are metered in at 65-70° C. The reaction mixture is stirred at 70° C. for a further 2 hours. The alcohols (ethanol and methanol) are removed at 300 mbar and 70° C. After addition of 150 g (8.33 mol) of water at 70° C., the lower aqueous phase is separated off. 100 g (5.56 mol) of water and 5 g (0.06 mol) of sodium bicarbonate are added at 70° C., and the lower aqueous phase is separated off. Azeotropic drying gives the target product (I-1) as a mixture (methyl and ethyl esters) in xylene. The product can be isolated at room temperature by filtration and drying. In a xylene/methanol mixture, the product (I-1) remains in solution. The yield is 98% of theory based on the compound of the formula (IIa-1).

Example 3

Partial Esterification 0.59 mol of the compound of the formula IIa-1 is initially charged in 566 g (4.90 mol) chlorobenzene. 71.6 g (2.24 mol) of methanol and 7.1 g (0.07 mol) of sulphuric acid 96% are metered in for the esterification. The mixture is heated to 70° C. and stirred at 70° C. for 4 hours. The mixture is then cooled to 40° C. and 25.4 g (0.30 mol) of sodium bicarbonate are added, with $CO_2$ being released. 368.9 g of water are added, and the reaction mixture is stirred at 60° C. for about half an hour. The lower product phase (methyl ester of the formula (I-1)) in chlorobenzene is separated off. Since the compound of the formula (I-1) does not remain dissolved at room temperature, the solvent chlorobenzene is replaced with dimethylacetamide.

The upper aqueous phase contains the unesterified compound of the formula (IIa-1), which is recycled and esterified. The yield is 89% of theory, based on the compound of the formula (IIa-1).

Example 4

Complete Esterification

At 70° C., 40 g (0.32 mol) of 32% strength aqueous sodium hydroxide solution are added to 400 g (0.5 mol) of cis-N-[(2,5-dimethyl)phenylacetyl]-1-amino-4-methoxycyclohexanecarboxylic acid (IIa-1) (39.9% in xylene). The water is removed by azeotropic distillation. At 70° C., 31 g (0.95 mol) of methanol are added. Over a period of about 2 hours, 52 g (0.55 mol) of methyl chloroformate (III-2) 99% are metered in at 70° C., with carbon dioxide being formed as waste gas. The reaction mixture is stirred at 70° C. for a further 2 hours. The alcohol (methanol) is removed at 100 mbar and 70° C. After addition of 120 g (6.7 mol) of water at 70° C., the lower aqueous phase is separated off. 80 g (4.4 mol) of water and 45 g (0.36 mol) of 32% strength aqueous sodium hydroxide solution are added at 70° C., and the lower aqueous phase is separated off. Azeotropic drying gives the target product (I'-1) as (methyl ester) in xylene. The product can be isolated at 20° C. by filtration and drying. In a xylene/methanol mixture, the product remains in solution. The yield is 92% of theory based on the compound of the formula (IIa-1).

Example 5

27.012 g (0.150 mol) of 30% NaOMe in methanol are added to 530.037 g (0.500 mol) of the compound of the formula IIa-1 30.1% in xylene. The methanol is distilled off under reduced pressure at 60° C. and 100 mbar. At 60° C., 52.498 g (0.550 mol) of methyl chloroformate (III-2) 99% are added dropwise over 1-2 hours, and the mixture is stirred at 60° C. for 0.5 hour. The compound of the formula (IX-1) is obtained from the reaction mixture as a crude product.

$^{13}$C-NMR (CD$_3$CN, 1.30 ppm): δ=181.9 (O—C=O), 162.8 (N=C—O), 135.1 (PheC—CH$_2$), 133.1 (Phe C—CH$_3$), 132.0 (Phe-C—H), 77.6 (H—C—OMe), 68.7 (=N—C—C=O), 56.3 (O—CH$_3$), 34.5 (N=C—CH2-Phe), 32.2 (CH$_2$—CH$_2$—C—N=), 27.6 (MeO—CH—CH$_2$), 20.3 (Phe-CH$_3$) ppm.

Owing to strong overlap with other components of the reaction mixture, four signals of the phenyl group could not be assigned.

Example 6

27.012 g (0.150 mol) of 30% NaOMe in methanol are added to 530.037 g (0.500 mol) of the compound of the formula IIa-1 30.1% in xylene. The methanol is distilled off under reduced pressure at 60° C. and 100 mbar. At 60° C., 52.498 g (0.550 mol) of methyl chloroformate (III-2) 99% are added dropwise over 1-2 hours, and the mixture is stirred at 60° C. for 0.5 hour.

Excess methyl chloroformate and residual alcohol are removed. 99 g (0.550 mol) of 30% NaOMe in MeOH are then metered in, and the mixture is stirred at 60° C. for 1 hour. This gives the enol (X-1).

The invention claimed is:
1. Process for preparing a compound of formula (I)

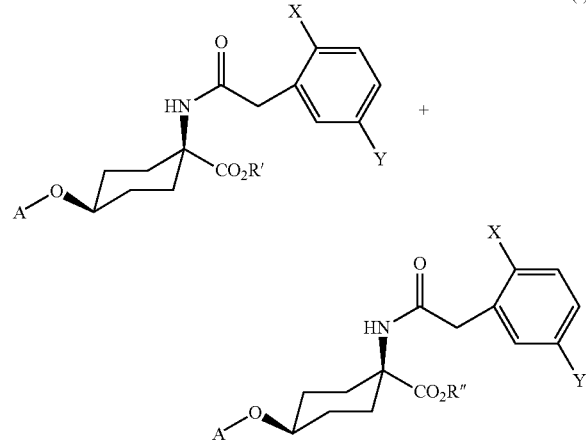

in which
X represents alkyl, halogen, alkoxy, haloalkyl or haloalkoxy,
Y represents hydrogen, alkyl, alkoxy, halogen, haloalkyl or haloalkoxy, where only one of the radicals X or Y may represent haloalkyl or haloalkoxy,
A represents $C_1$-$C_6$-alkyl,
R' represents alkyl,
R" represents alkyl,
comprising initially converting a compound of formula (IIa)

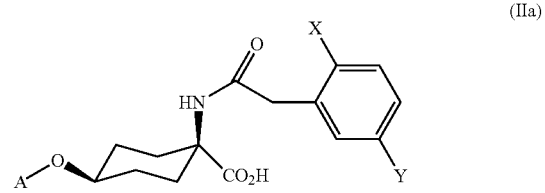

in the presence of a base into a compound of formula (IIb)

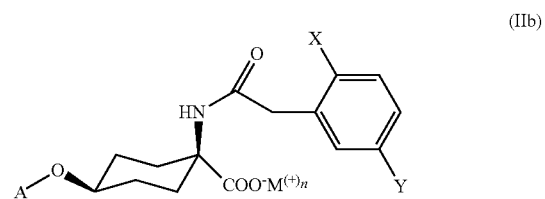

in which
M represents an alkali metal ion, an ion equivalent of an alkaline earth metal, an ion equivalent of aluminium or an ion equivalent of a transition metal or furthermore represents an ammonium ion where optionally one, two, three or all four hydrogen atoms may be replaced by identical or different radicals from the groups $C_1$-$C_5$-alkyl, $C_1$-$C_5$-isoalkyl or $C_3$-$C_7$-cycloalkyl, each of which may be mono- or polysubstituted by fluorine, chlorine, bromine, cyano, hydroxy or interrupted by one or more oxygen or sulphur atoms, or furthermore represents a cyclic secondary or tertiary aliphatic or heteroaliphatic ammonium ion, for example morpholinium, thiomorpholinium, piperidinium, pyrrolidinium, or in each case protonated 1,4-diazabicyclo[2.2.2]octane (DABCO) or 1,5-diazabicyclo[4.3.0]undec-7-ene (DBU), or furthermore represents a heterocyclic ammonium cation, for example in each case protonated pyridine, 2-methylpyridine, 3-methylpyridine, 4-methylpyridine, 2,4-dimethylpyridine, 2,5-di-methylpyridine, 2,6-dimethylpyridine, 5-ethyl-2-methylpyridine, pyrrole, imidazole, quinoline, quinoxaline, 1,2-dimethylimidazole, 1,3-dimethylimidazolium methylsulphate, or furthermore represents a sulphonium ion, or furthermore represents a magnesium halide cation, n represents the number 1 or 2, and reacted further with a compound of formula (III)

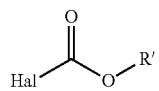

(III)

in which
Hal represents halogen,
to give a compound of formula (IV)

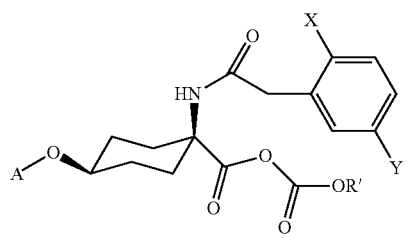

(IV)

in which X, Y, A and R' have the meanings given above, and
these are further cyclized to a compound of formula (IX)

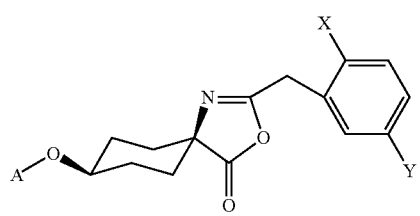

(IX)

in which X, Y and A have the meanings given above,
and these for their part are reacted with a compound of formula (V)

 (V)

in which R" has the meanings given above.

2. Process according to claim 1, where
X represents chlorine, bromine, methyl, ethyl, propyl, trifluoromethyl, methoxy, difluoromethoxy or trifluoromethoxy,
Y represents hydrogen, chlorine, bromine, methoxy, methyl, ethyl, propyl, trifluoromethyl or trifluoromethoxy, where only one of the radicals X or Y may represent trifluoromethyl, trifluoromethoxy or difluoromethoxy,
A represents $C_1$-$C_6$-alkyl,
Hal represents chlorine, bromine, fluorine, iodine,
R' represents $C_1$-$C_6$-alkyl,
R" represents $C_1$-$C_6$-alkyl.

3. Process according to claim 1, where
X represents chlorine, bromine, methyl, ethyl, methoxy, trifluoromethyl, trifluoromethoxy or difluoromethoxy,
Y represents chlorine, bromine, methyl, ethyl, propyl, methoxy, trifluoromethyl or trifluoromethoxy, where only one of the radicals X or Y may represent trifluoromethyl, trifluoromethoxy or difluoromethoxy,
A represents $C_1$-$C_4$-alkyl,
Hal represents chlorine, bromine or fluorine,
R' represents $C_1$-$C_4$-alkyl,
R" represents $C_1$-$C_4$-alkyl.

4. Process according to claim 1, where
X represents chlorine, bromine, methyl or trifluoromethyl,
Y represents chlorine, bromine or methyl,
A represents methyl, ethyl, propyl, butyl or isobutyl,
Hal represents chlorine or bromine,
R' represents methyl, ethyl, propyl, butyl or isobutyl,
R" represents methyl, ethyl, propyl, butyl or isobutyl.

5. Process according to claim 1, where
X represents methyl,
Y represents methyl,
A represents methyl,
Hal represents chlorine,
R' represents methyl or ethyl,
R" represents methyl or ethyl.

6. Process according to claim 1, where
X represents methyl,
Y represents methyl,
A represents methyl,
Hal represents chlorine,
R' represents ethyl,
R" represents methyl.

7. Process according to claim 1, where
M represents lithium, sodium, potassium, caesium, magnesium, calcium or represents an ammonium ion in which optionally one, two, three or all four hydrogen atoms may be replaced by identical or different radicals from the groups $C_1$-$C_5$-alkyl, $C_1$-$C_5$-isoalkyl or $C_3$-$C_7$-cycloalkyl, each of which may be mono- or polysubstituted by fluorine, chlorine, bromine, cyano, hydroxy and
n represents the number 1 or 2.

8. Process according to claim 1, where
M represents lithium, sodium, potassium, caesium, magnesium or calcium and
n represents the number 1 or 2.

9. Process according to claim 1, where
M represents lithium, sodium, potassium or caesium and
n represents the number 1.

10. Process according to claim 1, where
M represents sodium and
n represents the number 1.

11. Process according to claim 1, where the base employed is sodium carbonate.

12. Process according to claim 1, where the base employed is sodium methoxide.

13. Process according to claim 1, where the base employed is sodium hydroxide.

14. A Compound of formula (IX)

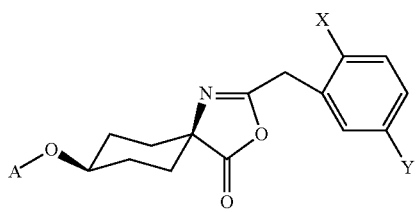

in which
X represents alkyl, halogen, alkoxy, haloalkyl or haloalkoxy,
Y represents hydrogen, alkyl, alkoxy, halogen, haloalkyl or haloalkoxy, where only one of the radicals X or Y may represent haloalkyl or haloalkoxy,
A represents $C_1$-$C_6$-alkyl,
R' represents alkyl,
R" represents alkyl,
M represents an alkali metal ion, an ion equivalent of an alkaline earth metal, an ion equivalent of aluminium or an ion equivalent of a transition metal or furthermore represents an ammonium ion where optionally one, two, three or all four hydrogen atoms may be replaced by identical or different radicals from the groups $C_1$-$C_5$-alkyl, $C_1$-$C_5$-isoalkyl or $C_3$-$C_7$-cycloalkyl, each of which may be mono- or polysubstituted by fluorine, chlorine, bromine, cyano, hydroxy or interrupted by one or more oxygen or sulphur atoms, or furthermore
represents a cyclic secondary or tertiary aliphatic or heteroaliphatic ammonium ion, for example morpholinium, thiomorpholinium, piperidinium, pyrrolidinium, or in each case protonated 1,4-diazabicyclo[2.2.2]octane (DABCO) or 1,5-diazabicyclo[4.3.0]undec-7-ene (DBU), or furthermore
represents a heterocyclic ammonium cation, for example in each case protonated pyridine, 2-methylpyridine, 3-methylpyridine, 4-methylpyridine, 2,4-dimethylpyridine, 2,5-di-methylpyridine, 2,6-dimethylpyridine, 5-ethyl-2-methylpyridine, pyrrole, imidazole, quinoline, quinoxaline, 1,2-dimethylimidazole, 1,3-dimethylimidazolium methylsulphate, or furthermore
represents a sulphonium ion, or furthermore
represents a magnesium halide cation,
n represents the number 1 or 2.

15. Process for preparing a compound of formula (I')

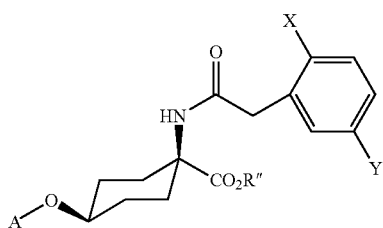

in which
X represents alkyl, halogen, alkoxy, haloalkyl or haloalkoxy,
Y represents hydrogen, alkyl, alkoxy, halogen, haloalkyl or haloalkoxy, where only one of the radicals X or Y may represent haloalkyl or haloalkoxy,
A represents $C_1$-$C_6$-alkyl,
R' represents alkyl,
R" represents alkyl,
wherein initially a compound of formula (IIa)

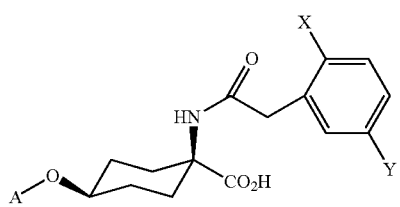

is converted in the presence of a base into a compound of formula (IIb)

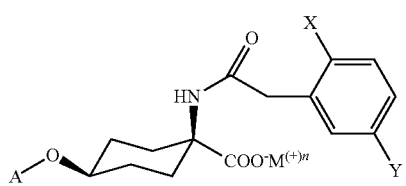

in which
X represents alkyl, halogen, alkoxy, haloalkyl or haloalkoxy,
Y represents hydrogen, alkyl, alkoxy, halogen, haloalkyl or haloalkoxy, where only one of the radicals X or Y may represent haloalkyl or haloalkoxy,
A represents $C_1$-$C_6$-alkyl,
R' represents alkyl,
R" represents alkyl,
M represents an alkali metal ion, an ion equivalent of an alkaline earth metal, an ion equivalent of aluminium or an ion equivalent of a transition metal or furthermore
represents an ammonium ion where optionally one, two, three or all four hydrogen atoms may be replaced by identical or different radicals from the groups $C_1$-$C_5$-alkyl, $C_1$-$C_5$-isoalkyl or $C_3$-$C_7$-cycloalkyl, each of which may be mono- or polysubstituted by fluorine, chlorine, bromine, cyano, hydroxy or interrupted by one or more oxygen or sulphur atoms, or furthermore
represents a cyclic secondary or tertiary aliphatic or heteroaliphatic ammonium ion, for example morpholinium, thiomorpholinium, piperidinium, pyrrolidinium, or in each case protonated 1,4-diazabicyclo[2.2.2]octane (DABCO) or 1,5-diazabicyclo[4.3.0]undec-7-ene (DBU), or furthermore
represents a heterocyclic ammonium cation, for example in each case protonated pyridine, 2-methylpyridine, 3-methylpyridine, 4-methylpyridine, 2,4-dimethylpyridine, 2,5-di-methylpyridine, 2,6-dimethylpyridine, 5-ethyl-2-methylpyridine, pyrrole, imidazole, quinoline, quinoxaline, 1,2-dimethylimidazole, 1,3-dimethylimidazolium methylsulphate, or furthermore
represents a sulphonium ion, or furthermore
represents a magnesium halide cation,
n represents the number 1 or 2, and reacted further with a compound of formula (III)
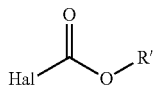
(III)
in which
Hal represents halogen,
to give a compound of formula (IV)
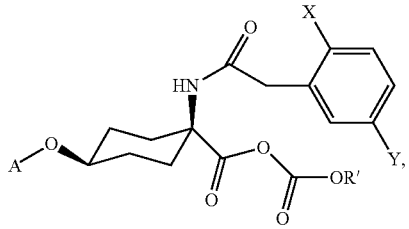
(IV)
and which is further cyclized to a compound of formula (IX)
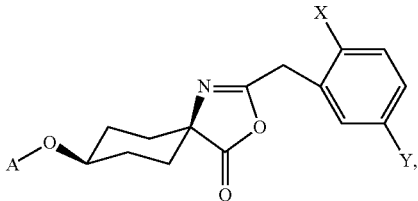
(IX)
and these for their part are reacted with a compound of formula (V)
R''—OH  (V).
* * * * *